US011850133B2

(12) United States Patent
Jenkins et al.

(10) Patent No.: US 11,850,133 B2
(45) Date of Patent: Dec. 26, 2023

(54) PATTERNING OF AN ELASTIC LAMINATE

(71) Applicant: Kimberly-Clark Worldwide, Inc., Neenah, WI (US)

(72) Inventors: Shawn E. Jenkins, Suwanee, GA (US); David W. Primm, Cumming, GA (US); Chris M. Allen, Lawrenceville, GA (US); Howard M. Welch, Woodstock, GA (US); David J. Reader, Appleton, WI (US); Steven W. Fitting, Acworth, GA (US); Vikram S. Kaul, Atlanta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 204 days.

(21) Appl. No.: 17/416,039

(22) PCT Filed: Dec. 16, 2019

(86) PCT No.: PCT/US2019/066631
§ 371 (c)(1),
(2) Date: Jun. 18, 2021

(87) PCT Pub. No.: WO2020/131747
PCT Pub. Date: Jun. 25, 2020

(65) Prior Publication Data
US 2022/0062069 A1    Mar. 3, 2022

Related U.S. Application Data

(60) Provisional application No. 62/783,196, filed on Dec. 20, 2018.

(51) Int. Cl.
*B32B 7/05*    (2019.01)
*A61F 13/513*    (2006.01)
(Continued)

(52) U.S. Cl.
CPC .......... *A61F 13/513* (2013.01); *B29C 66/344* (2013.01); *B29C 70/56* (2013.01);
(Continued)

(58) Field of Classification Search
CPC ...... B32B 2310/0831; B32B 2307/412; B32B 2037/1253; B32B 37/24; B32B 37/12;
(Continued)

(56) References Cited

U.S. PATENT DOCUMENTS 5,143,774 A    9/1992  Cancio et al.
5,229,186 A    7/1993  Tribble et al.
(Continued)

FOREIGN PATENT DOCUMENTS

CN    103957855 A    7/2014
GB    2252528 A1    8/1992

OTHER PUBLICATIONS

CONWED, "How To Use Conwed Netting in Production Processes", CONWED Global Netting Solutions, http://www.conwedplastics.com/en/about/plastic-netting-101/create-superior-composites/.

*Primary Examiner* — Vishal I Patel

(57) ABSTRACT

The present disclosure discloses an embossed patterned elastic laminate. The elastic laminate has an embossed pattern of at least three surface areas. The current disclosure also includes a process for making an embossed patterned elastic laminate. The embossed patterned elastic laminate provides a permanent change to visual aesthetic without adversely impacting the elastic film.

10 Claims, 3 Drawing Sheets

INFUSE SABBEL EMBOSSED AT Rm TEMP    INFUSE SABBEL EMBOSSED AT 180F

(51) Int. Cl.
  *B32B 5/02* (2006.01)
  *B32B 5/04* (2006.01)
  *B32B 37/00* (2006.01)
  *B32B 37/14* (2006.01)
  *B32B 38/06* (2006.01)
  *B29C 65/00* (2006.01)
  *B29C 70/56* (2006.01)
  *A61F 13/51* (2006.01)
  *A61F 13/511* (2006.01)

(52) U.S. Cl.
  CPC ............ *B32B 5/022* (2013.01); *B32B 5/04* (2013.01); *B32B 7/05* (2019.01); *B32B 37/0084* (2013.01); *B32B 37/144* (2013.01); *B32B 38/06* (2013.01); *A61F 2013/51083* (2013.01); *A61F 2013/51178* (2013.01); *A61F 2013/51322* (2013.01); *A61F 2013/51361* (2013.01); *B32B 2305/20* (2013.01); *B32B 2307/51* (2013.01); *B32B 2307/514* (2013.01); *B32B 2307/718* (2013.01); *B32B 2309/02* (2013.01); *B32B 2309/16* (2013.01); *B32B 2555/00* (2013.01)

(58) Field of Classification Search
  CPC ............ B32B 27/06; G02F 1/133331; A61F 2013/51361; A61F 2013/51322; A61F 2013/51178; A61F 2013/51083
  See application file for complete search history.

(56) References Cited

U.S. PATENT DOCUMENTS

| | | |
|---|---|---|
| 5,259,902 A | 11/1993 | Muckenfuhs |
| 5,882,769 A | 3/1999 | McCormack et al. |
| 6,096,668 A | 8/2000 | Abuto et al. |
| 6,114,263 A | 9/2000 | Benson et al. |
| 6,193,701 B1 * | 2/2001 | Van Gompel ..... A61F 13/49009 604/385.27 |
| 8,647,553 B2 | 2/2014 | Kobayashi et al. |
| 8,759,606 B2 | 6/2014 | Bond et al. |
| 9,327,477 B2 * | 5/2016 | Muslet .................. B32B 27/32 |
| 2004/0102125 A1 | 5/2004 | Morman et al. |
| 2010/0310810 A1 | 12/2010 | Bond et al. |
| 2012/0116342 A1 | 5/2012 | Stjernholm et al. |
| 2014/0272357 A1 * | 9/2014 | He .......................... B32B 27/12 524/427 |
| 2014/0343522 A1 * | 11/2014 | Arai .................... A61F 13/4902 604/385.16 |
| 2016/0129626 A1 | 5/2016 | Arora et al. |
| 2017/0000663 A1 | 1/2017 | Xu et al. |
| 2018/0092785 A1 | 4/2018 | Zink et al. |

* cited by examiner

PATTERNING OF AN ELASTIC LAMINATE

TECHNICAL FIELD

This application claims priority from U.S. provisional Patent Application Ser. No. 62/783,196 filed on 20 Dec. 2018, the entire contents of which are incorporated herein by reference.

The present disclosure discloses an embossed patterned elastic laminate. The elastic laminate has an embossed pattern of at least three surface areas. The current disclosure also includes a process for making an embossed patterned elastic laminate. The embossed patterned elastic laminate provides a permanent change to visual aesthetic without adversely impacting the elastic film.

BACKGROUND OF THE DISCLOSURE

Elastomeric materials have the ability to expand to fit over or around an object and then retract to provide a snug fit around the object. Elastomeric materials may be used in garments to provide a snug fit, such as in active wear. Elastomeric materials can also form resilient and effective barriers, such as in the cuffs of thermal garments intended to retain body heat.

One example of a type of garment where both fit and barrier properties are important is personal hygienic products such as diapers. Elastomeric materials may be used in the waist, around the leg openings, and in the fasteners (for a diaper) or sides (for an underpants-type garment). The elastomeric materials in these areas may improve the overall fit of the garment, and also make it much easier to both don and remove the garment. The elastomeric materials also act as resilient barriers, improving the containment capabilities of the garment while still allowing comfort and free movement to the wearer.

Elastomeric materials may be expensive and producing thin films of expensive material can therefore reduce cost. However, producing thin films may be complicated due to tearing and pinholing.

There remains a need for a more cost effective elastomeric film, or an inexpensive laminate of an elastomeric film that is bonded to one or more layers of substrate, such as fabric. There also remains a need for an elastomeric film or laminate that has good elastomeric properties, such as permanent set. Such a film or laminate can be suitable for improving the fit and comfort of garments and personal care items, including limited-use and disposable items.

As such, utilizing meltblown or spunbond facings with sufficient elasticity, groovability, comfort, and softness may be used in absorbent article applications where minimal fiber pullout and durability are desired.

SUMMARY OF THE DISCLOSURE

The current disclosure discloses permanent change to the visual aesthetic of an embossed patterned elastic laminate film without adversely impacting it. As disclosed herein, impact on elastic properties may be mitigated by taking advantage of the releasability of fibers at embossed points. Furthermore, embossing, which may be done on a converting line, alters the visual appearance and increases the modulus and peel strength of the laminate. When stretched, the modulus drops to match that of the unembossed material, but the visual impact and improved peel strength remain.

One embodiment of the disclosure pertains to an elastic embossed laminate includes an elastomeric pleated film material that includes a first, second and third surface area. The first surface area includes facing material that is bonded to an elastic layer. The second surface area is where the laminate is embossed. The third surface area is the area that is not in the first or second surface areas where the second surface area has a bulk of at least less than 10% of the bulk of the third surface area. Furthermore, the fibers in the second surface area have been at least temporarily melt fused together causing flattening of fiber cross-section with individual fibers still present and the film remains unapertured in the second surface area.

A further embodiment of the present disclosure discloses a process for making an elastic embossed laminate. The elastic embossed laminate includes pleated facing layers where the layers are thermally point bonded to an elastic layer with a bond roll that imparts a first pattern while the elastic layer is in the stretched state. The elastic laminate also includes embossing rolls that impart a second pattern while the elastic laminate is in the relaxed state. The elastic laminate also includes bonding rolls that are heated to a temperature of at least 30 degrees Fahrenheit higher than the temperature of the embossing rolls.

The above summary of the present disclosure is not intended to describe each embodiment or every implementation of the present disclosure. Advantages and attainments, together with a more complete understanding of the disclosure, will become apparent and appreciated by referring to the following detailed description and claims taken in conjunction with the accompanying drawings.

BRIEF DESCRIPTION OF DRAWINGS

The disclosure may be more completely understood in consideration of the following detailed description of various embodiments in connection with the accompanying drawings, in which.

DETAILED DESCRIPTION OF THE DISLOSURE

Figure 1B:
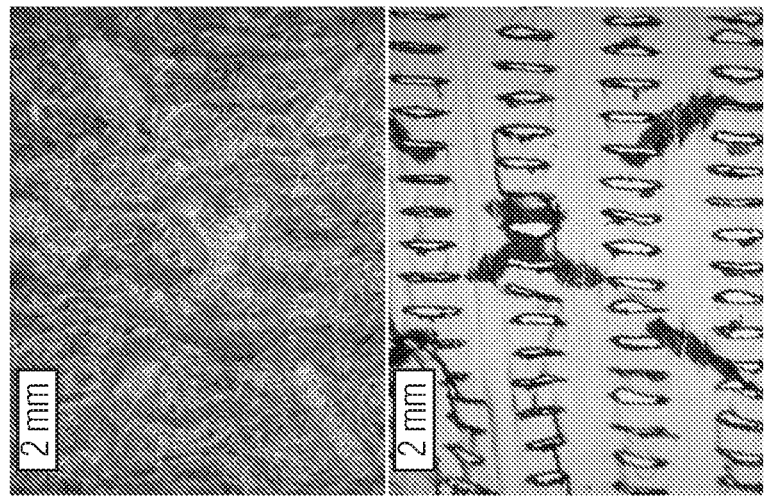
FIG. 1B depicts an embossed SABBEL at 180 degrees Fahrenheit.

When introducing elements of the present disclosure or the preferred embodiment(s) thereof, the articles "a", "an", and "the" are intended to mean that there are one or more of the elements.

As used herein, the terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

As used herein, the terms "machine direction" or "MD" generally refers to the direction in which a material is produced. The term "cross-machine direction" or "CD" refers to the direction perpendicular to the machine direction.

As used herein, the term "nonwoven" generally refers to a web having a structure of individual fibers or threads which are interlaid, but not in an identifiable manner as in a knitted fabric. Examples of suitable nonwoven fabrics or webs include, but are not limited to, meltblown webs, spunbond webs, bonded carded webs, airlaid webs, coform webs, hydraulically entangled webs, and so forth.

As used herein, the term "meltblown" generally refers to a nonwoven web that is formed by a process in which a molten thermoplastic material is extruded through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that are substantially continuous or discontinuous, generally smaller than 10 microns in diameter, and generally tacky when deposited onto a collecting surface.

As used herein, the term "spunbond" generally refers to a web containing small diameter substantially continuous fibers. The fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spunbond webs is described and illustrated, for example, in U.S. Pat. No. 3,338,992 to Kinney, U.S. Pat. No. 3,341,394 to Kinney, U.S. Pat. No. 3,502,538 to Levy, U.S. Pat. No. 3,502,763 to Hartman, U.S. Pat. No. 3,542,615 to Dobo, et al., U.S. Pat. No. 3,692,618 to Dorschner, et al., U.S. Pat. No. 3,802,817 to Matsuki, et al., U.S. Pat. No. 4,340,563 to Appel, et al., and U.S. Pat. No. 5,382,400 to Pike et al., which are incorporated herein in their entirety by reference thereto for all purposes. Spunbond fibers are generally not tacky when they are deposited onto a collecting surface. As such, the fibers may be bonded together after deposition onto a collecting surface in order to integrate the fibers. Spunbond fibers may sometimes have diameters less than about 40 microns, and are often between about 5 to about 20 microns.

As used herein, the term "elastomeric" and "elastic" and refers to a material that, upon application of a stretching force, is stretchable in at least one direction (such as the CD direction), and which upon release of the stretching force, contracts/returns to approximately its original dimension. For example, a stretched material may have a stretched length that is at least 50 percent greater than its relaxed unstretched length, and which will recover to within at least 50 percent of its stretched length upon release of the stretching force. A hypothetical example would be a one (1) inch sample of a material that is stretchable to at least 1.50 inches and which, upon release of the stretching force, will recover to a length of not more than 1.25 inches. Desirably, the material contracts or recovers at least 50 percent, and even more desirably, at least 80 percent of the stretched length.

As used herein, the term "film" refers to a thermoplastic film made using a film extrusion process, such as a cast film or blown film extrusion process. The term includes apertured films, slit films, and other porous films which constitute liquid transfer films, as well as films which do not transfer liquid. "Film" further refers to material in a sheet-like form where the dimensions of the material in the x (length) and y (width) directions are substantially larger than the dimension in the z (thickness) direction.

As used herein, the term "polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

As used herein, the term "strand" refers to an article of manufacture whose width is less than a film and is suitable for incorporating into a film, according to the present invention. More particularly, a strand may be thread-like with a cylindrical cross-section, for example, or may be flat or ribbon-like with a rectangular cross-section, for example.

As used herein, the term "vertical filament stretch-bonded laminate" or "VF SBL" refers to a stretch-bonded laminate made using a continuous vertical filament process, as described herein.

As used herein, the term "laminate" refers to a layered structure of sheet-like materials stacked and bonded so that the layers are substantially coextensive across the width of the narrowest sheet of material. The layers may comprise films, fabrics, other materials in sheet form, or combinations thereof. For instance, a laminate may be a structure comprising a layer of film and a layer of fabric bonded together across their width such that the two layers remain bonded as a single sheet under normal use. A laminate may also be called a composite or a coated material. "Laminate" as a verb refers to the process by which such a layered structure is formed.

As used herein, "stretchable" and "recoverable" are descriptive terms used herein to describe the elastomeric properties of a material. "Stretchable" means that the material can be extended by a pulling force to a specified dimension significantly greater than its initial dimension without breaking. For example, a material that is 10 cm long that can be extended to about 13 cm long without breaking under a pulling force could be described as stretchable. "Recoverable" means that a material which is extended by a pulling force to a certain dimension significantly greater than its initial dimension without breaking will return to its initial dimension or a specified dimension that is adequately close to the initial dimension when the pulling force is released. For example, a material that is 10 cm long that can be extended to about 13 cm long without breaking under a pulling force, and which returns to about 10 cm long or to a specified length that is adequately close to 10 cm could be described as recoverable.

As used herein, "film strength" or "mechanical strength" are the tensile properties of a film or laminate, as measured by ASTM D-822 "Tensile Properties of Thin Plastic Sheeting." Unless noted otherwise, "film strength" or "mechanical strength" refers specifically to tensile at break and percent elongation at break.

As used herein, "tear strength" is a property of a film which determines the ease or difficulty by which the film can be torn starting from a notch or aperture cut into the film, as measured by the notched Elmendorf test, ASTM D-1922.

As used herein, "bond strength" is a property of a laminate comprising two or more layers. The bond strength is determined by measuring the force required to peel apart the laminate layers after they are bonded together. Bond strength can be measured by methods such as ASTM D-1876 or ASTM F-904.

As used herein, "pinholing" refers to the formation of small holes or tears in a film while the film is being formed, laminated, activated, or other manufacturing or processing step. "Pinholes" are the small holes or tears so formed. Pinholes are typically in the range of about 100 micro m to 1 cm in size.

As used herein, "SBC" refers to styrenic block copolymers.

Generally speaking, the present disclosure discloses multilayer elastomeric film having a polyolefin-based layer. The multilayer film may have a total of, for example, of at least three layers, four layers, five layers, six layers, seven layers, or eight or more layers. The elastomeric film can also be part of a laminate formed with one or more substrates, such as nonwoven fabrics.

The elastomeric film may optionally comprise other components that, in some instances, modify the film properties, aid in the processing of the film, or modify the appearance of the film. Viscosity-reducing polymers and plasticizers can be added as processing aids. High-density polyethylene can be added to help prevent age-related degradation of the other polymers. Other additives such as pigments, dyes, antioxidants, antistatic agents, slip agents, foaming agents, heat stabilizers, light stabilizers, inorganic fillers, organic fillers or combinations thereof can be added. The amounts of these components relative to the layer weight can be about 0.1 weight (wt) percent, about 0.5 wt percent, about 1 wt percent, about 2 wt percent, about 5 wt percent, about 7 wt percent, or about 10 wt percent.

Any film-forming process may be used to prepare the elastomeric film. For example, any blending process, such as melt blending, can be used. Also, any extrusion process, such as cast extrusion or blown-film extrusion can be used to form the film. If the elastomeric film is a multilayer film, the film can be formed by a coextrusion process.

In some embodiments, the elastomeric film layers comprise polymers that are inherently sticky or tacky. When such elastomeric films are extruded and wound into a roll, the film can sometimes stick to itself or "block," sometimes becoming difficult or impossible to unwind. Blocking can become more pronounced as the film is aged or stored in a warm environment, such as inside a storage warehouse. This blocking problem can be addressed in a number of ways, if desired. For example, antiblocking agents, such as powdered inorganic materials (e.g., silica or talc) can be incorporated within layers of the film. Antiblocking agents can also be dusted onto the outer surfaces of extruded film as the film is being formed. The elastomeric film can also be surface-coated with materials that are not sticky, such as a nonblocking polymer, a brittle nonblocking polymer, a surface coating such as a lacquer or ink, or other such coatings.

In a further embodiment of the present invention, the elastomeric film may be three or more layers of a multilayer film. In some embodiments of a three layer film, the film may be a coextruded multilayer film with an ABC-type construction. In the ABC-type construction, the A layer and the C layer can be the same or different composition. The A layer and the C layer form the outer layers of the film, which are sometimes referred to as the "skin," "surface," or "capping" layers. The B layer, that is also referred to as the "core" or "central" layer, is the layer that comprises one or more elastomeric polymers—the elastomeric polymer can be an olefin-based elastomeric polymer, a nonolefin elastomeric polymer, or combinations thereof. Where the A layer and the C layer are the same composition, this provides an ABA-type construction.

In some aspects of the invention, the polyolefin-based layer(s) (e.g., the skin layer(s)) can improve the processability of the elastomeric film, even when the second layer (e.g., the core layer) comprises a less-processable polymer (e.g., a styrene block copolymer). Also, olefin-based elastomeric polymers in the skin layer of the film can provide a greater affinity for an olefin-based substrate (e.g., polyolefin fabric) bonded to the surface of the film in a laminate. This greater affinity can improve the overall bond between the film surface and the substrate (e.g., fabric fibers).

The multilayer elastomeric film may have a basis weight of no more than about 40 grams per square meter (gsm) and can be, for example, about 0.1 gsm, about 0.25 gsm, about 0.5 gsm, about 0.75 gsm, about 1 gsm, about 2 gsm, about 3 gsm, about 4 gsm, about 5 gsm, about 6 gsm, about 7 gsm, about 8 gsm, about 9 gsm, about 10 gsm, about 11 gsm, about 12 gsm, about 13 gsm, about 14 gsm, about 15 gsm, about 16 gsm, about 17 gsm, about 18 gsm, about 19 gsm, about 20 gsm, about 21 gsm, about 22 gsm, about 23 gsm, about 24 gsm, about 25 gsm, about 30 gsm, about 35 gsm, about 36 gsm, about 37 gsm, about 38 gsm, about 39 gsm, or about 40 gsm. In some instances, the basis weight is at least about 0.1 gsm, at least about 0.5 gsm, at least about 1 gsm, or at least about 2 gsm. The basis weight can be no more than about 39 gsm, no more than about 35 gsm, no more than about 30 gsm, or no more than about 25 gsm. In some embodiments, addition of an effective amount of one or more draw down polymers to one or more layers can provide the aforementioned basis weights, including, for example, no more than about 40 gsm, no more than about 35 gsm, no more than about 30 gsm, or no more than about 25 gsm.

The permanent set of the multilayer elastomeric film after recovery from being stretched to 100 percent of its original length of the multilayer elastomeric film can be no more than about 15 percent and can be, for example, about 0.5 percent, about 1 percent, about 2 percent, about 3 percent, about 4 percent, about 5 percent, about 6 percent, about 7 percent, about 8 percent, about 9 percent, about 10 percent, about 11 percent, about 12 percent, about 13 percent, about 14 percent, or about 15 percent. The permanent set of the multilayer elastomeric film after recovery from being stretched to 100 percent of its original length can be at least about 0.5 percent, at least about 1 percent, or at least about 2 percent. The permanent set of the multilayer elastomeric film after recovery from being stretched to 100 percent of its original length can be no more than about 14 percent, no more than about 10 percent, or no more than about 7 percent. In some instances, the aforementioned permanent set is for multilayer elastomeric films prior to activation, and in other instances the aforementioned permanent set is for multilayer elastomeric films after activation. In some embodiments, addition of an effective amount of elastomeric polymer (i.e., olefin-based elastomeric polymer, nonolefin-based elastomeric polymer, or combinations thereof) to one or more layers can provide the aforementioned permanent set, including, for example, no more than about 15 percent, no more than about 10 percent, or no more than about 7 percent.

The multilayer elastomeric film may, in some embodiments, be made at extrusion line speeds as discussed above for the monolayer elastomeric film. The compositions of the layers may confer processing properties that allow extrusion at line speeds described herein.

One or more layers of the elastomeric film may optionally comprise other components that, in some instances, modify the film properties, aid in the processing of the film, or modify the appearance of the film. Viscosity-reducing polymers and plasticizers can be added as processing aids. High-density polyethylene can be added to help prevent age-related degradation of the other polymers. Other additives such as pigments, dyes, antioxidants, antistatic agents, slip agents, foaming agents, heat stabilizers, light stabilizers, inorganic fillers, organic fillers or combinations thereof can be added. The amounts of these components relative to the layer weight can be about 0.1 wt percent, about 0.5 wt percent, about 1 wt percent, about 2 wt percent, about 5 wt percent, about 7 wt percent, or about 10 wt percent. These additives can be present in one, several, or all layers of a multilayer elastomeric film.

In another aspect of the invention, the elastomeric multilayer film may include antiblocking agents or other methods/components to address blocking problems associate with layers having polymers that are inherently sticky or tacky, as discussed in more detail above.

Furthermore, as discussed above, any suitable blending method may be used to blend the components of the layers together. Also, any extrusion process, such as cast extrusion or blown-film extrusion can be used to form the multilayer elastomeric film. By extruding films comprising olefin-based elastomeric polymers or, alternatively, skins comprising olefin-based elastomeric polymers, the processability of the elastomeric film can be improved. And the problems sometimes associated with low basis weight films (e.g., fluctuating basis weights, draw resonance, web tear-offs, etc.) can be reduced or eliminated. The multilayer films described herein can be easier to manufacture when the skin layer(s) comprise(s) olefin-based elastomeric polymers, even when there is a high concentration of elastomeric polymers (e.g., SBCs) in the core layer.

The elastomeric films described herein can also be used to form a laminate. Such a laminate includes one or more substrate layers and the elastomeric film (e.g., monolayers or multilayers). The substrate layer may be an extensible material including but not limited to another polymer film, fabric, nonwoven fabric, woven fabric, knitted fabric, scrim, or netting. The elastomeric film can be bonded to substrate layers on one or both sides.

When two or more substrate layers are used to make the laminate, the substrate layers may be the same or different extensible material. The composition of the substrate layers may be the same or different, even when the same extensible material is used (e.g., two nonwoven layers where one nonwoven layer is made from polyolefin and the other nonwoven layer is made from polyester).

The substrate layer (e.g., nonwoven fabrics) may have a basis weight of about 3 gsm, about 4 gsm, about 5 gsm, about 7 gsm, about 9 gsm, about 10 gsm, about 15 gsm, about 20 gsm, about 25 gsm, about 30 gsm, about 40 gsm, about 50 gsm, about 75 gsm, about 100 gsm, about 150 gsm, or about 200 gsm. The basis weight of the substrate layer (e.g., nonwoven fabrics) can be at least about 3 gsm, at least about 5 gsm, or at least about 10 gsm. The basis weight of the substrate layer can be no more than about 10 gsm, no more than about 20 gsm, no more than about 30 gsm, no more than about 50 gsm, no more than about 75 gsm, no more than about 100 gsm, or no more than about 200 gsm. If two substrate layers are used, one layer can have a basis weight that is the same or different from the other.

In some embodiments, the substrate layer is a nonwoven fabric. For example, the substrate layer may be spunbond nonwoven webs, carded nonwoven webs (e.g., thermally bonded, adhesively bonded, or spunlaced), meltblown nonwoven webs, spunlaced nonwoven webs, spunbond meltblown spunbond nonwoven webs, spunbond meltblown spunbond nonwoven webs, unbonded nonwoven webs, electrospun nonwoven webs, flashspun nonwoven webs (e.g., TYVEK™ by DuPont), or combinations thereof. These fabrics can comprise fibers of polyolefins such as polypropylene or polyethylene, polyesters, polyamides, polyurethanes, elastomers, rayon, cellulose, copolymers thereof, or blends thereof or mixtures thereof. The nonwoven fabrics can also comprise fibers that are homogenous structures or comprise bicomponent structures such as sheath/core, side-by-side, islands-in-the-sea, and other bicomponent configurations. For a detailed description of some nonwovens, see "Nonwoven Fabric Primer and Reference Sampler" by E. A. Vaughn, Association of the Nonwoven Fabrics Industry, 3d Edition (1992). Such nonwoven fabrics can have a basis weight of at least about 3 gsm, at least about 5 gsm, at least about 10 gsm, no more than about 30 gsm, no more than about 75 gsm, no more than about 100 gsm, or no more than about 150 gsm.

The nonwoven fabrics may include fibers or can be made from fibers that have a cross section perpendicular to the fiber longitudinal axis that is substantially non-circular. Substantially non-circular means that the ratio of the longest axis of the cross section to the shortest axis of the cross section is at least about 1.1. The ratio of the longest axis of the cross section to the shortest axis of the cross section can be about 1.1, about 1.2, about 1.5, about 2.0, about 3.0, about 6.0, about 10.0, or about 15.0. In some embodiments, this ratio can be at least about 1.2, at least about 1.5, or at least about 2.0. These ratios can be, for example, no more than about 3.0, no more than about 6.0, no more than about 10.0, or no more than about 15.0.

The shape of the cross section perpendicular to the fiber longitudinal axis of the substantially non-circular fibers can be rectangular (e.g., with rounded corners) which are also referred to as "flat" fibers, trilobal, or oblong (e.g., oval) in the cross section. These substantially non-circular fibers can provide more surface area to bond to the elastomeric film than nonwoven fabrics with fibers that are circular in cross section. Such an increase in surface area can increase the bond strength between the elastomeric film and fibers.

Bond strength between the elastomeric film and the substrate layers of the laminate can be measured by any number of test methods, including, for example, ASTM D-1876. In some embodiments, optimum bond strength is a balance between bond strength that is too low (e.g., that can lead to delamination of the film from the substrate) and bond strength that is too high (e.g., that can lead to inelastic behavior of the laminate, even when activated). Bonding between the layers can be achieved by any method, including, but not limited to, adhesive bonding, extrusion lamination, thermal bonding, ultrasonic bonding, calendering, point bonding, laser bonding, and combinations thereof. The bonding strength can depend on the bonding method and variations within a given bonding method. For example, for layers bonded by an adhesive, the choice of adhesive and the amount of adhesive applied to bond the layers can be adjusted to achieve the desired bond strength.

Bonding can also occur between the substrate layer (e.g., nonwoven) and the elastomeric film during extrusion by heating the film to be molten; this molten film is pressed into the substrate layer to embed the substrate into the film to create bonding. In some instances, this bonding can be enhanced if the chemical composition of the elastomeric film has a chemical affinity for the chemical composition of the substrate layer. Of course, if the elastomeric film is a multilayer film, chemical affinity relative to the substrate layer relates to the layer of the multilayer film that is in contact with the substrate. Similarly, if the substrate is a multilayer substrate or a bicomponent substrate, chemical affinity relative to the film relates to the substrate component that is in contact with the film.

In a further aspect of the invention, the temperature of the extruded molten elastomeric web can be controlled. For example, when the extruded film is of thin gauge, the extruded web has less mass to retain heat during the extrusion process. Less mass can result in an extruded molten polymer web that can solidify rapidly. An extruded polymer film that solidifies too rapidly can sometimes result in weaker bond strength because less embedding of the substrate in the extruded elastomeric film can occur. In some instances, the bond strength is further decreased when the extruded polymer does not have great chemical affinity for the materials that comprise the substrate.

In another aspect, film layers comprising SBC do not have strong natural chemical affinity for the polyolefinic substrate materials. To maintain bonding in these instances, sheets of films comprising SBC and substrates with fibers sometimes rely on mechanical bonding forces, such as those achieved by embedding the substrate fibers into the surface of the film. If the film has solidified before contacting the substrate, the fibers cannot be sufficiently embedded into the solidified surface of the film. Hence, the bond strength between the film and substrate of the laminate can be poor, and the elastomeric material can sometimes delaminate easily. Bond strength can be enhanced by other bonding means, such as application of an adhesive. In other embodiments, bond strength can be enhanced by using a multilayer film that includes one layer with a less compatible polymer (e.g., SBC) and one or more layers with a polymer that is more compatible (e.g., an olefin-based elastomeric polymer).

In other aspects of the invention, elastic laminates having films comprising elastomers that are chemically similar to the substrate composition may have increased bonding strength when the substrate is embedded into the film during extrusion. For example, films comprising polyolefins can have chemical affinity for substrates that comprise polyolefins and can therefore have increased bonding strength. In some instances, the chemical affinity (e.g., when the film and the substrate comprise polyolefins) can provide substantial bonding even if there is little or no mechanical bonding (e.g., from embedded fibers in the film). In some instances, if the film is soft or semi-molten when it contacts the substrate, this can lead to enhanced bonding via mechanical bonding. Of course, other methods of bonding (e.g., adhesive bonding) can be used to increase bonding strength.

In some instances, olefin-based elastomeric films do not solidify as rapidly as SBC-based materials. The extruded olefin-based elastomeric web can be semi-molten and soft when it contacts the nonwoven fibers, which allows the fibers to embed into the surface. Hence, olefin-based elastomeric films, or multilayer elastomeric films with olefin-based elastomeric skins, can form laminates with stronger bond strength and less tendency to delaminate.

In other instances, the chemical affinity of the elastomeric film may be sufficiently high that an acceptable bond strength is obtained, but the laminate may be difficult to activate due to a number of factors that may include, for example, the intimate coupling of the nonwoven substrate and the film which can hinder the activation process. The high chemical affinity of the elastomeric film for the nonwoven can sometimes result in roll blocking and thus can sometimes cause problems in storing, transporting, and unwinding of the laminate. Such roll blocking can be addressed by appropriate measures as described herein or by any appropriate method.

Laminates of elastomeric films and fabrics are particularly suited to activation by incremental stretching. As disclosed in the commonly-assigned U.S. Pat. No. 5,422,172 ("Wu '172"), which is incorporated by reference, laminates of the sort made here can be activated by incremental stretching using the incremental stretching rollers described therein.

Polyethylenes that may be used to form the nonwoven facing layer include conventional polyethylene and low density polyethylene (LDPE). Other suitable ethylene polymers are available from The Dow Chemical Company under the designations ASPUN™ (LLDPE), DOWLEX™ (LLDPE) and ATTANET™ (ULDPE). Other suitable ethylene polymers are described in U.S. Pat. No. 4,937,299 to Ewen, et al., U.S. Pat. No. 5,218,071 to Tsutsui et al., U.S. Pat. No. 5,272,236 to Lai, et al., and U.S. Pat. No. 5,278,272 to Lai, et al., which are incorporated herein in their entirety by reference thereto for all purposes.

In addition, polyethylene-based plastomers may be used in conjunction with the aforementioned polyethylenes when forming the spunbond or meltblown nonwoven facing layer. Such ethylene-based plastomers include ethylene-based copolymer plastomers available under the designation EXACT™ from ExxonMobil Chemical Company of Houston, Tex. Other suitable polyethylene plastomers are available under the designation ENGAGE™ and AFFINITY™ from Dow Chemical Company of Midland, Mich. An additional suitable polyethylene-based plastomer is an olefin block copolymer available from Dow Chemical Company of Midland, Mich. under the trade designation INFUSE™.

Of course, the present disclosure is by no means limited to the use of ethylene polymers. For instance, conventional polypropylene can be a component of the spunbond or meltblown nonwoven facing layer. Further, propylene plastomers may also be suitable for use in the nonwoven facing layers in combination with conventional polypropylene. Suitable plastomeric propylene polymers may include, for instance, copolymers or terpolymers of propylene, copolymers of propylene with an a-olefin (e.g., $C_3$-$C_{20}$), such as ethylene, 1-butene, 2-butene, the various pentene isomers, 1-hexene, 1-octene, 1-nonene, 1-decene, 1-unidecene, 1-dodecene, 4-methyl-1-pentene, 4-methyl-1-hexene, 5-methyl-1-hexene, vinylcyclohexene, styrene, etc. The comonomer content of the propylene polymer may be about 35 weight percent or less, in some embodiments from about 1 weight percent to about 20 weight percent, and in some embodiments, from about 2 weight percent to about 10 weight percent. Preferably, the density of the polypropylene (e.g., propylene/a-olefin copolymer) may be 0.91 g/cm³ or less, in some embodiments, from 0.85 g/cm³ to 0.88 g/cm³, and in some embodiments, from 0.85 g/cm³ to 0.87 g/cm³. Suitable propylene polymers are commercially available under the designations VISTAMAXX™ (e.g., 6102), a propylene-based elastomer from ExxonMobil Chemical Co. of Houston, Tex.; FINA™ (e.g., 8573) from Atofina Chemicals of Feluy, Belgium; TAFMER™ available from Mitsui Petrochemical Industries; and VERSIFY™ available from Dow Chemical Co. of Midland, Mich. Other examples of suitable propylene polymers are described in U.S. Pat. No. 5,539,056 to Yang, et al., U.S. Pat. No. 5,596,052 to Resconi, et al., and U.S. Pat. No. 6,500,563 to Datta, et al., which are incorporated herein in their entirety by reference thereto for all purposes.

Regardless of the particular combination of polyolefins and/or polyolefin-based plastomers employed in the nonwoven facing layer(s) of the present disclosure, a polyolefin can be present in the nonwoven facing layer(s) in an amount up to about 100 percent, such as an amount ranging from about 40 weight percent to about 100 weight percent, such as an amount ranging from about 50 weight percent to about 99 weight percent, such as an amount ranging from about 60 weight percent to about 98 weight percent based on the total weight of the nonwoven facing layer(s). Meanwhile, a polyolefin-based plastomer can be present in the nonwoven facing layer(s) in an amount ranging from about 0.5 weight percent to about 60 weight percent, such as from about 1 weight percent to about 50 weight percent, such as from about 2 weight percent to about 40 weight percent based on total weight of the nonwoven facing layers.

If desired, the nonwoven facing used to form the elastic nonwoven laminate of the present invention may have a multi-layer structure. Suitable multi-layered materials may include, for instance, spunbond/meltblown/spunbond (SMS) laminates and spunbond/meltblown (SM) laminates. Various examples of suitable SMS laminates are described in U.S. Pat. No. 4,041,203 to Brock et al., U.S. Pat. No. 4,374,888 to Bornslaeger, U.S. Pat. No. 4,766,029 to Brock et al., U.S. Pat. No. 5,169,706 to Collier et al., U.S. Pat. No. 5,213,881 to Timmons et al., and U.S. Pat. No. 5,464,688 to Timmons, et al., which are incorporated herein in their entirety by reference thereto for all purposes. In addition, commercially available SMS laminates may be obtained from Kimberly-Clark Corporation under the designations Spunguard® and Evolution®.

Another example of a multi-layered structure is a spunbond web produced on a multiple spin bank machine in which a spin bank deposits fibers over a layer of fibers deposited from a previous spin bank. Such an individual spunbond nonwoven facing may also be thought of as a multi-layered structure. In this situation, the various layers of deposited fibers in the nonwoven web may be the same, or they may be different in basis weight and/or in terms of the composition, type, size, level of crimp, and/or shape of the fibers produced. As another example, a single nonwoven facing may be provided as two or more individually produced layers of a spunbond web, a meltblown web, etc., which have been bonded together to form the nonwoven facing. These individually produced layers may differ in terms of production method, basis weight, composition, etc. as discussed above.

The basis weight of each of the nonwoven facing layers may generally vary, such as from about 1 gsm to about 120 gsm, such as from about 5 gsm to about 80 gsm, such as from about 10 gsm to about 60 gsm, such as from about 15 gsm to about 40 gsm. When multiple nonwoven facings are utilized, such materials may have the same or different basis weights.

Generally, as a result of the techniques discussed herein, spunbond or meltblown nonwoven facings containing a polypropylene homopolymer with a polypropylene-based elastomer or a polyethylene homopolymer with a polyethylene-based elastomer. The elastomers can provide the nonwoven facing with the desired level of softness, while at the same time allowing for easier grooving of the nonwoven facing compared to if only polypropylene or polyethylene are utilized, which is a possibility although such facings would be more loosely configured or fuzzy. Because the grooving of such nonwoven facings is easier to accomplish, there is less risk of damaging an underlying elastic film in laminates containing the aforementioned nonwoven facings.

In reference to spunbond nonwoven facings particularly, incorporating an ethylene-based elastomer such as INFUSE™ or a polypropylene-based elastomer such as VERSIFY™ with a polyethylene or a polypropylene creates a softer nonwoven facing that can be more easily grooved than a nonwoven facing containing polyethylene as the only olefinic polymer. Likewise, incorporating a polypropylene-based elastomer such as VISTAMAXX™ with a polypropylene can create a softer nonwoven facing that can be more easily grooved compared to a nonwoven facing containing polypropylene as the only olefinic polymer.

Further, in reference to meltblown nonwoven facings in particular, because meltblown facings generally include polymers having a lower molecular weight than other facings and also are less tacky and not bonded when initially formed, which means that meltblown facings can be grooved more easily. Moreover, polypropylene meltblown facings can be grooved more easily than polyethylene meltblown facings because polypropylene is more brittle than polyethylene, which is softer. In addition, post-bonding of polyethylene-based meltblown facings can be carried out at lower temperatures and pressures because of their lower molecular weights compared to spunbond facings and facings based on polymers other than polyethylene.

However, regardless of whether the facings of the present invention are polyethylene-based, polypropylene-based, spunbond, or meltblown, the film components, facing components, grooving conditions, and bonding conditions can be selected to achieve an elastic nonwoven laminate that has the desired levels of softness and elasticity with reduced fuzziness, while at the same exhibiting enhanced hook engagement and resisting fiber pullout, such as when the elastic nonwoven laminates are used in absorbent article applications utilizing hook or tab fastening means. For instance, when a tab or hook is attached to a laminate of the present invention that has been post bonded with smooth rolls, the elongation at failure (percent elongation) of the tab or hook, which corresponds with hook disengagement, can range from about 50 percent to about 200 percent, such as from about 75 percent to about 190 percent, such as from about 100 percent to about 180 percent. Likewise, when a tab or hook is attached to a laminate of the present invention that has been post-bonded using a wire-weave pattern, the elongation at failure (percent elongation) of the tab or hook can range from about 50 percent to about 150 percent, such as from about 60 percent to about 125 percent, such as from about 70 percent to about 100 percent.

Further, when a tab or hook is attached to a laminate of the present invention that has been post bonded with smooth rolls, the load at failure can range from about 600 grams-force to about 2200 grams-force, such as from about 800 grams-force to about 2100 grams-force, such as from about 1000 grams-force to about 2000 grams-force. Meanwhile, when a tab or hook is attached to a laminate of the present invention that has been post-bonded using a wire-weave pattern, the load at failure can range from about 400 grams-force to about 1200 grams-force, such as from about 500 grams-force to about 1100 grams-force, such as from about 600 grams-force to about 1000 grams-force.

The components of the elastic nonwoven laminates of the present invention may also be selectively controlled to achieve the desired tensile properties. For instance, elastic nonwoven laminates post-bonded with smooth rolls can exhibit a percent elongation of greater than about 200 percent, such as greater than about 400 percent, such as greater than about 800 percent. Further, elastic nonwoven laminates post-bonded using a wire-weave pattern can exhibit a percent elongation of greater than about 200 percent, such as from about 200 percent to about 1000 percent, such as from about 400 percent to about 800 percent. In addition, elastic nonwoven laminates post-bonded using a wire-weave pattern can exhibit a load at failure of greater than about 3000 grams-force, such as greater than about 4000 grams-force, such as greater than about 5000 grams-force. Meanwhile, elastic nonwoven laminates post-bonded using a wire-weave pattern can exhibit a load at failure of from about 1000 grams-force to about 4250 grams-force, such as from about 1500 grams-force to about 4000 grams-force, such as from about 2000 grams-force to about 3750 grams-force.

Further, the elastic nonwoven laminates of the present invention can exhibit a load loss of less than about 60 percent, such as from about 10 percent to about 60 percent, such as from about 15 percent to about 55 percent, such as from about 30 percent to about 50 percent, which is indicative that even with post-bonding, the elastic nonwoven laminates of the present invention maintain their elastic properties.

It is also to be understood that the elastic nonwoven laminates of the present disclosure may also include one or more frangible layers located outside the one or more of the facings layers or disposed between the one or more facing layers and the elastic strand. Such frangible layers are described in U.S. patent application Ser. No. 13/720,194, filed on Dec. 19, 2012, which is incorporated herein in its entirety by reference thereto for all purposes. Generally, the frangible layer can also be grooved in the manner described in reference to the nonwoven facings. The frangible layer can be used to add loftiness to the elastic nonwoven laminates of the present invention or to achieve the desired aesthetics depending on the particular application.

The elastic nonwoven laminate of the present invention may be used in a wide variety of applications. For example, the elastic nonwoven laminate may be used in an absorbent article. An "absorbent article" generally refers to any article capable of absorbing water or other fluids. Examples of some absorbent articles include, but are not limited to, personal care absorbent articles, such as diapers, training pants, absorbent underpants, incontinence articles, feminine hygiene products (e.g., sanitary napkins), swim wear, baby wipes, and so forth; medical absorbent articles, such as garments, fenestration materials, underpads, bedpads, bandages, absorbent drapes, and medical wipes; food service wipers; clothing articles; and so forth. Materials and processes suitable for forming such absorbent articles are well known to those skilled in the art. Absorbent articles may include a substantially liquid-impermeable layer (e.g., outer cover), a liquid-permeable layer (e.g., bodyside liner, surge layer, etc.), and an absorbent core. In one particular embodiment, the elastic nonwoven laminate of the present invention may have a wide variety of other uses, such as in providing an elastic waist, leg cuff/gasketing, stretchable ear, side panel, outer cover, or any other component in which elastic properties are desirable.

For elastic film based laminates, experiments have been done with SABBEL (both INFUSE-based and VIS-TAMAXX-based) and NBL. The NBL has a different look than the SABBEL. MD stretch laminates and CD and biaxial stretch laminates are disclosed herein.

Figure 1A:
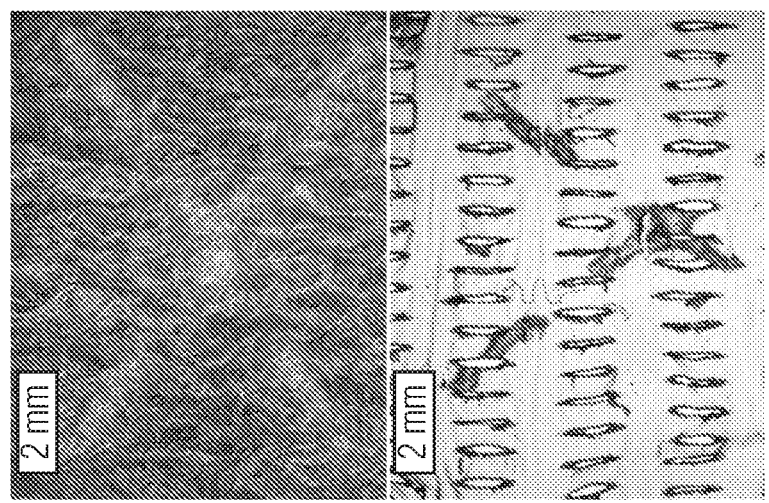
FIG. 1A depicts an embossed SABBEL at room temperature.
Figure 2A:
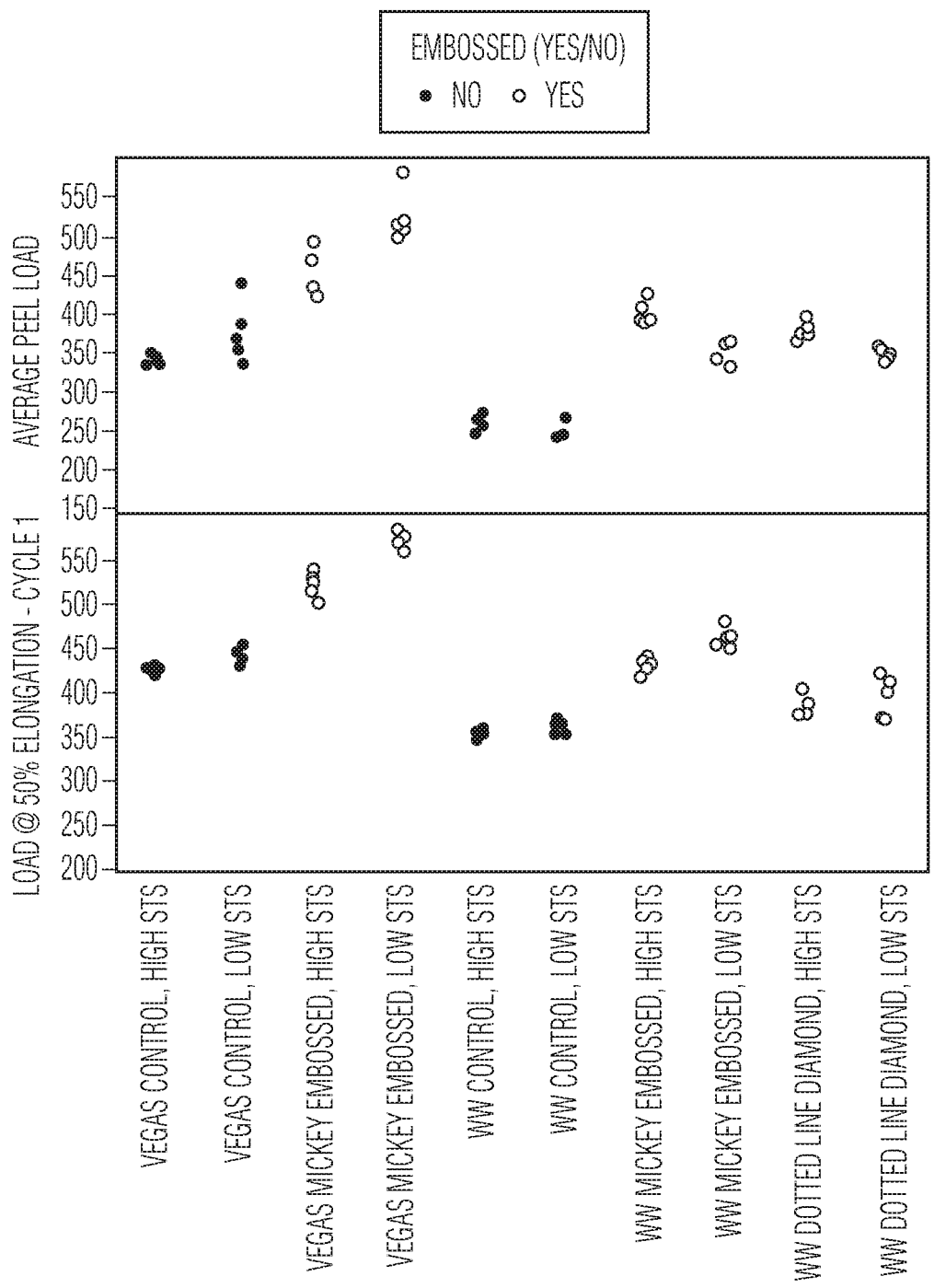
FIG. 2A shows property differences of embossed SABBEL before stretching.

Utilizing embossed SABBEL the film remains intact at embossed points. This will allow for the possibility to regain elastomeric properties after stretching such as after fibers release from the film. FIG. 1A depicts Infuse SABBEL embossed at room temperature. FIG. 2A depicts infuse SABBEL at 180 degrees Fahrenheit.

Figure 2B:
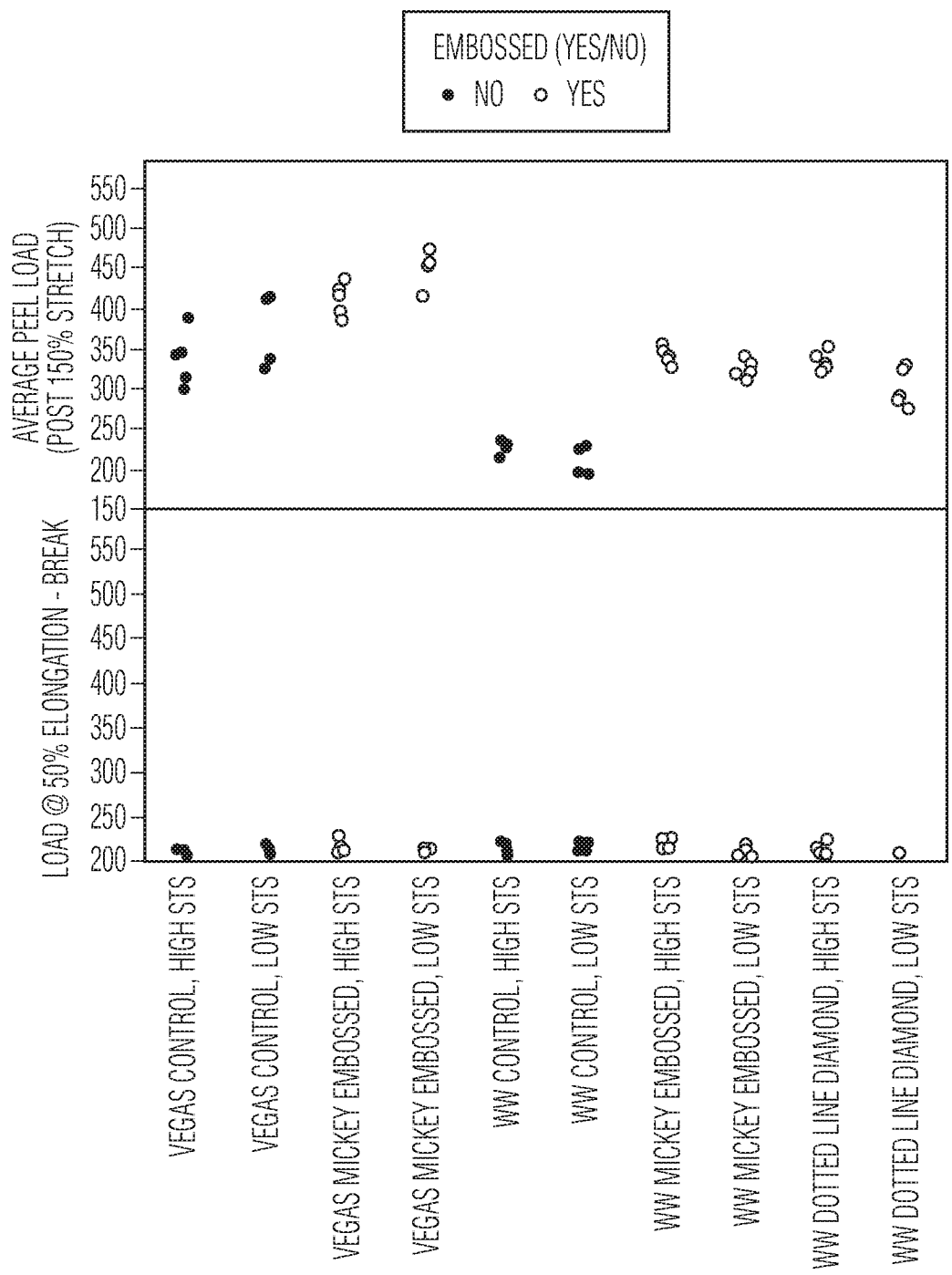
FIG. 2B shows property differences of embossed SABBEL after stretching.

It has also been found that the peel strength of embossed material is greater than that of an un-embossed material even after stretching where not all fibers are released from film. For example, in view of FIGS. 2A and 2B, the property differences found in embossed SABBEL are evident. Before stretching peel strength is higher after embossing. However, the extension tension is also higher after embossing. However, after stretching the stretching lowers extension tension. It has also been found that embossing creates deeper channels in bulkier laminates. Also differences between minimum and maximum points grow after stretching.

Thickness of the material changes after stretching as well. Thickness diminishes closer to the core. However up to about 40% of the thickness is regained by stretching or retracting wherein more bulk is regained in material closer to the core.

First Embodiment

In a first embodiment the invention provides for an elastic embossed laminate comprising: an elastomeric pleated film material comprising a first, second and third surface areas comprising: (i) first surface area comprising a facing material that is bonded to an elastic layer; (ii) second surface area comprising an embossed laminate; and (iii) third surface area wherein the third surface area is not in the first or second surface areas and wherein the second surface area has a bulk density of less than about 10% of the bulk density of the third surface area and wherein the fibers in the second surface area have been at least temporarily melt fused together resulting in a flattened fiber cross-section wherein individual fibers and the elastomeric pleated film material remain unapertured in the second surface area.

The method according to the preceding embodiment, wherein the first, second and third surface areas comprises a nonwoven fabric.

The method according to the preceding embodiments, wherein the first, second or third surface areas comprises a nonwoven fabric selected from the group consisting of spunbond nonwoven webs, carded nonwoven webs, meltblown nonwoven webs, spunlaced nonwoven webs, spunbond meltblown spunbond nonwoven webs, spunbond meltblown meltblown spunbond nonwoven webs, unbonded nonwoven webs, and combinations thereof.

The method according to the preceding embodiments, wherein the first, second and third surface areas have a basis weight of from about 1 gsm to about 100 gsm.

The method according to the preceding embodiments, wherein the nonwoven fabric comprises fibers with a cross section perpendicular to the fiber longitudinal axis.

The method according to the preceding embodiments, wherein the nonwoven fabric comprises fibers with a cross section perpendicular to the fiber longitudinal axis having a longest axis and a shortest axis wherein the ratio of the length of the longest axis to the length of the shortest axis is from about 1.1 to about 15.0.

The method according to the preceding embodiments, wherein the elastomeric pleated film material occurs using adhesive bonding, thermal bonding, extrusion lamination, ultrasonic bonding, calendaring or combinations thereof.

The method according to the preceding embodiments, wherein the elastomeric pleated material is activated after stretching the material by using incremental stretching.

The method according to the preceding embodiments, wherein the elastomeric pleated material comprises at least one non-styrenic elastomeric polymer that is present in a combined amount of from about 70 percent by weight to about 90 percent by weight percent of the elastomeric pleated material.

The method according to the preceding embodiments, wherein the elastic embossed laminate is stretched in a machine-direction, cross-machine direction, biaxial stretch or canted disk direction.

The method according to the preceding embodiments, wherein the elastic embossed laminate comprising a multi-layer elastomeric film according to claim 1.

The method according to the preceding embodiments, wherein the elastic embossed laminate is used in an absorbent article.

Second Embodiment

In a second embodiment the invention provides for a process for making an elastic embossed laminate comprising:
thermally point bonding pleated facing layers to an elastic layer with a bonding roll that imparts a first pattern while the elastic layer is in the stretched state;
embossing an elastic laminate with embossing rolls that impart a second pattern while the elastic laminate is in the relaxed state;
heating the bonding rolls to a temperature of at least 30 degrees F. higher than the temperature of the embossing rolls.

The process according to the preceding embodiment, wherein the first, second or third surface areas comprises a nonwoven fabric. The bonding rolls and embossed rolls are different.

The process according to the preceding embodiments, wherein the first, second or third surface areas comprises a nonwoven fabric selected from the group consisting of spunbond nonwoven webs, carded nonwoven webs, meltblown nonwoven webs, spunlaced nonwoven webs, spunbond meltblown spunbond nonwoven webs, spunbond meltblown meltblown spunbond nonwoven webs, unbonded nonwoven webs, and combinations thereof.

The process according to the preceding embodiments, wherein the first, second or third surface areas have a basis weight of from about 1 gsm to about 100 gsm.

The process according to the preceding embodiments, wherein the nonwoven fabric comprises fibers with a cross section perpendicular to the fiber longitudinal axis.

The process according to the preceding embodiments, wherein the nonwoven fabric comprises fibers with a cross section perpendicular to the fiber longitudinal axis having a longest axis and a shortest axis and the ratio of the length of the longest axis to the length of the shortest axis is about 1.1 to about 15.0.

The process according to the preceding embodiments, wherein the elastic embossed laminate process occurs using adhesive bonding, thermal bonding, extrusion lamination, ultrasonic bonding, calendaring or combinations thereof.

The process according to the preceding embodiments, wherein the process is activated after incremental stretching.

The process according to the preceding embodiments, wherein at least one non-styrenic elastomeric polymer is present in a combined amount of from 70 percent weight percent to 90 weight percent of said film.

The process according to the preceding embodiments, wherein the elastic embossed laminate is stretched in a machine direction, cross-machine direction, biaxial stretch or canted disk direction.

The process according to the preceding embodiments, wherein the elastic embossed laminate is used in an absorbent article.

What is claimed is:

1. A process for making an elastic embossed laminate comprising:
thermally point bonding a facing layer to an elastic layer with a bonding roll to imparts a first pattern while the elastic layer is in the stretched state to at least partially form an elastic laminate having a first peel strength;
embossing the elastic laminate with embossing rolls to impart a second pattern while the elastic laminate is in the relaxed state to at least partially form embossments on the embossed elastic laminate, wherein the embossed elastic laminate has a second peel strength greater than the first peel strength;
heating the bonding rolls to a temperature of at least 30 degrees Fahrenheit higher than the temperature of the embossing rolls, wherein the embossed elastic laminate has a greater load capacity at 50% elongation than the elastic laminate.

2. The process of claim 1, wherein the facing layer comprises a nonwoven fabric.

3. The process of claim 2, wherein the facing layer comprises a nonwoven fabric selected from the group consisting of spunbond nonwoven webs, carded nonwoven webs, meltblown nonwoven webs, spunlaced nonwoven webs, spunbond meltblown spunbond nonwoven webs, spunbond meltblown meltblown spunbond nonwoven webs, unbonded nonwoven webs, and combinations thereof.

4. The process of claim 1, wherein the facing layer has a basis weight of from 1 gsm to 100 gsm.

5. The process of claim 4, wherein the nonwoven fabric comprises fibers with a cross section perpendicular to the fiber longitudinal axis.

6. The process of claim 4, wherein the nonwoven fabric comprises fibers with a cross section perpendicular to the fiber longitudinal axis having a longest axis and a shortest axis and the ratio of the length of the longest axis to the length of the shortest axis is 1.1 to 15.0.

7. The process of claim 1, wherein the process for making the elastic embossed laminate is activated after using incremental stretching.

8. The process of claim 1, wherein at least one non-styrenic elastomeric polymer is present in a combined amount of from 70 percent weight percent to 90 weight percent of said film.

9. The process of claim 1, wherein the elastic embossed laminate is stretched in a machine direction, cross-machine direction, biaxial stretch or canted disk direction.

10. The process according to claim 1, wherein the embossed elastic laminate is used in an absorbent article.

\* \* \* \* \*